(12) United States Patent
Warner

(10) Patent No.: US 9,269,119 B2
(45) Date of Patent: Feb. 23, 2016

(54) DEVICES AND METHODS FOR HEALTH TRACKING AND PROVIDING INFORMATION FOR IMPROVING HEALTH

(71) Applicant: SONY CORPORATION, Tokyo (JP)

(72) Inventor: Jason Michael Warner, San Diego, CA (US)

(73) Assignee: Sony Corporation, Tokyo (JP)

( * ) Notice: Subject to any disclaimer, the term of this patent is extended or adjusted under 35 U.S.C. 154(b) by 119 days.

(21) Appl. No.: 14/160,871

(22) Filed: Jan. 22, 2014

(65) Prior Publication Data

US 2015/0206413 A1 Jul. 23, 2015

(51) Int. Cl.
*G08B 23/00* (2006.01)
*G06Q 50/22* (2012.01)
(Continued)

(52) U.S. Cl.
CPC .............. *G06Q 50/22* (2013.01); *A61B 5/0205* (2013.01); *A61B 5/1118* (2013.01); *A61B 5/6803* (2013.01); *A61B 5/6804* (2013.01); *A61B 5/6898* (2013.01); *G06F 19/3481* (2013.01);
(Continued)

(58) Field of Classification Search
CPC .... G06Q 50/22; A61B 5/6803; A61B 5/6898; A61B 5/0205; A61B 5/6804; A61B 5/14532; A61B 5/11; A61B 5/02438; A61B 5/749; A61B 5/14546; A61B 5/1118; G06F 3/13; G06F 3/167; G06F 19/30; A63B 24/00
USPC ......... 340/573.1, 521, 539.1, 539.11, 539.12, 340/539.13, 5.52, 1.1, 5.1; 700/91
See application file for complete search history.

(56) References Cited

U.S. PATENT DOCUMENTS 4,278,095 A 7/1981 Lapeyre
4,566,461 A 1/1986 Lubell et al.
(Continued)

FOREIGN PATENT DOCUMENTS

JP H08241496 A 9/1996
JP H10281790 A 10/1998
(Continued)

OTHER PUBLICATIONS

Julia Anne Framel, Aravind Babu Asam, Guru Prashanth Balasubramanian, Takeshi Suzuki, Charles D. Hedrick Jr., "User Device Position Indication for Security and Distributed Race Challenges", File History of related U.S. Appl. No. 13/644,044, filed Oct. 3, 2012.
(Continued)

*Primary Examiner* — Anh V La
(74) *Attorney, Agent, or Firm* — John L. Rogitz; John M. Rogitz

(57) ABSTRACT

In one aspect, a device includes at least one storage medium bearing instructions executable by a processor, and at least one processor configured for accessing the storage medium to execute the instructions to configure the processor for receiving input pertaining to at least a first health parameter, monitoring at least one biometric of a user, and determining whether the user's biometric conforms to the first health parameter. The instructions also configure the processor for providing an indication that the biometric conforms to the first health parameter in response to determining that the user's biometric conforms to the first health parameter, and providing a recommendation for conforming to the first health parameter in response to determining that the user's biometric does not conform to the first health parameter.

18 Claims, 4 Drawing Sheets

(51) Int. Cl.
*A61B 5/11* (2006.01)
*A61B 5/00* (2006.01)
*A61B 5/0205* (2006.01)
*G06F 19/00* (2011.01)
*A61B 5/024* (2006.01)
*A61B 5/145* (2006.01)
*A63B 24/00* (2006.01)
*G06F 3/16* (2006.01)
*G06F 3/01* (2006.01)

(52) U.S. Cl.
CPC ............ *A61B 5/02438* (2013.01); *A61B 5/11* (2013.01); *A61B 5/14532* (2013.01); *A61B 5/14546* (2013.01); *A61B 5/749* (2013.01); *A63B 24/00* (2013.01); *G06F 3/017* (2013.01); *G06F 3/167* (2013.01)

(56) References Cited

U.S. PATENT DOCUMENTS

| | | |
|---|---|---|
| 4,625,962 A | 12/1986 | Street |
| 4,708,337 A | 11/1987 | Shyu |
| 4,728,100 A | 3/1988 | Smith |
| 4,869,497 A | 9/1989 | Stewart et al. |
| 4,916,628 A | 4/1990 | Kugler |
| 4,920,969 A | 5/1990 | Suzuki et al. |
| 5,072,458 A | 12/1991 | Suzuki |
| 5,111,818 A | 5/1992 | Suzuki et al. |
| 5,207,621 A | 5/1993 | Koch et al. |
| 5,277,197 A | 1/1994 | Church et al. |
| 5,314,389 A | 5/1994 | Dotan |
| 5,410,472 A | 4/1995 | Anderson |
| 5,433,683 A | 7/1995 | Stevens |
| 5,454,770 A | 10/1995 | Stevens |
| 5,474,083 A | 12/1995 | Church et al. |
| 5,474,090 A | 12/1995 | Begun et al. |
| 5,516,334 A | 5/1996 | Easton |
| 5,524,637 A | 6/1996 | Erickson |
| 5,579,777 A | 12/1996 | Suga |
| 5,598,849 A | 2/1997 | Browne |
| 5,704,067 A | 1/1998 | Brady |
| 5,706,822 A | 1/1998 | Khavari |
| 5,857,939 A | 1/1999 | Kaufman |
| 5,921,891 A | 7/1999 | Browne |
| 6,013,007 A | 1/2000 | Root et al. |
| 6,032,108 A | 2/2000 | Seiple et al. |
| 6,042,519 A | 3/2000 | Shea |
| 6,050,924 A | 4/2000 | Shea |
| 6,101,443 A | 8/2000 | Kato et al. |
| 6,106,297 A | 8/2000 | Pollak et al. |
| 6,171,218 B1 | 1/2001 | Shea |
| 6,198,431 B1 | 3/2001 | Gibson |
| 6,220,865 B1 | 4/2001 | Macri et al. |
| 6,231,527 B1 | 5/2001 | Sol |
| 6,244,988 B1 | 6/2001 | Delman |
| 6,251,048 B1 | 6/2001 | Kaufman |
| 6,259,944 B1 | 7/2001 | Margulis et al. |
| 6,296,595 B1 | 10/2001 | Stark et al. |
| 6,447,424 B1 | 9/2002 | Ashby et al. |
| 6,447,425 B1 | 9/2002 | Keller et al. |
| 6,464,618 B1 | 10/2002 | Shea |
| 6,497,638 B1 | 12/2002 | Shea |
| 6,500,100 B1 | 12/2002 | Harrell |
| 6,515,593 B1 | 2/2003 | Stark et al. |
| 6,582,342 B2 | 6/2003 | Kaufman |
| 6,601,016 B1 | 7/2003 | Brown et al. |
| 6,605,044 B2 | 8/2003 | Birnbaum |
| 6,638,198 B1 | 10/2003 | Shea |
| 6,659,916 B1 | 12/2003 | Shea |
| 6,659,946 B1 | 12/2003 | Batchelor et al. |
| 6,672,991 B2 | 1/2004 | O'Malley |
| 6,702,719 B1 | 3/2004 | Brown et al. |
| 6,746,371 B1 | 6/2004 | Brown et al. |
| 6,749,537 B1 | 6/2004 | Hickman |
| 6,786,848 B2 | 9/2004 | Yamashita et al. |
| 6,793,607 B2 | 9/2004 | Neil |
| 6,863,641 B1 | 3/2005 | Brown et al. |
| 6,866,613 B1 | 3/2005 | Brown et al. |
| 6,882,883 B2 | 4/2005 | Condie et al. |
| 6,997,882 B1 | 2/2006 | Parker et al. |
| 7,024,369 B1 | 4/2006 | Brown et al. |
| 7,056,265 B1 | 6/2006 | Shea |
| 7,057,551 B1 | 6/2006 | Vogt |
| 7,070,539 B2 | 7/2006 | Brown et al. |
| 7,128,693 B2 | 10/2006 | Brown et al. |
| 7,192,401 B2 | 3/2007 | Saalasti et al. |
| 7,223,215 B2 | 5/2007 | Bastyr |
| 7,227,468 B1 | 6/2007 | Florio |
| 7,245,254 B1 | 7/2007 | Vogt |
| 7,328,612 B2 | 2/2008 | Jämsen et al. |
| 7,351,187 B2 | 4/2008 | Seliber |
| 7,370,763 B1 | 5/2008 | Pascucci |
| 7,376,423 B2 | 5/2008 | Sakanaba |
| 7,438,670 B2 | 10/2008 | Gray et al. |
| 7,507,183 B2 | 3/2009 | Anderson et al. |
| 7,586,418 B2 | 9/2009 | Cuddihy et al. |
| 7,617,615 B1 | 11/2009 | Martorell et al. |
| 7,633,076 B2 | 12/2009 | Huppi et al. |
| 7,664,292 B2 | 2/2010 | Van Den et al. |
| 7,683,252 B2 | 3/2010 | Oliver et al. |
| 7,699,752 B1 | 4/2010 | Anderson et al. |
| 7,728,214 B2 | 6/2010 | Oliver et al. |
| 7,786,856 B2 | 8/2010 | O'Brien |
| 7,840,031 B2 | 11/2010 | Albertson et al. |
| 7,841,966 B2 | 11/2010 | Aaron et al. |
| 7,857,730 B2 | 12/2010 | Dugan |
| 7,894,849 B2 * | 2/2011 | Kass .................... A61B 5/0002 340/521 |
| 7,931,563 B2 | 4/2011 | Shaw et al. |
| 7,951,046 B1 | 5/2011 | Barber, Jr. |
| 7,966,230 B2 | 6/2011 | Brown |
| 7,979,136 B2 | 7/2011 | Young et al. |
| 7,996,080 B1 | 8/2011 | Hartman et al. |
| 8,021,270 B2 | 9/2011 | D'eredita |
| 8,029,410 B2 | 10/2011 | Shea |
| 8,047,965 B2 | 11/2011 | Shea |
| 8,057,360 B2 | 11/2011 | Shea |
| 8,062,182 B2 | 11/2011 | Somers |
| 8,092,346 B2 | 1/2012 | Shea |
| 8,103,762 B2 | 1/2012 | Duberry |
| 8,109,858 B2 | 2/2012 | Redmann |
| 8,125,314 B2 * | 2/2012 | Fithian .................... G06Q 10/00 340/1.1 |
| 8,157,730 B2 | 4/2012 | LeBoeuf et al. |
| 8,162,802 B2 | 4/2012 | Berg |
| 8,182,424 B2 | 5/2012 | Heckerman |
| 8,199,014 B1 | 6/2012 | Kindeberg |
| 8,204,786 B2 | 6/2012 | Leboeuf et al. |
| 8,219,191 B1 | 7/2012 | Hartman et al. |
| 8,277,377 B2 | 10/2012 | Quy |
| 8,317,658 B2 | 11/2012 | Dorogusker et al. |
| 8,333,874 B2 | 12/2012 | Currie |
| 8,343,012 B2 | 1/2013 | Redmann |
| 8,360,785 B2 | 1/2013 | Park et al. |
| 8,360,935 B2 | 1/2013 | Olsen et al. |
| 8,371,990 B2 | 2/2013 | Shea |
| 8,406,085 B2 | 3/2013 | Sakita |
| 8,435,177 B2 | 5/2013 | Lanfermann et al. |
| 8,452,413 B2 | 5/2013 | Young et al. |
| 8,467,860 B2 | 6/2013 | Salazar et al. |
| 8,491,446 B2 | 7/2013 | Hinds et al. |
| 8,512,209 B2 | 8/2013 | Guidi et al. |
| 8,512,548 B2 | 8/2013 | Bar-or et al. |
| 8,514,067 B2 | 8/2013 | Hyde et al. |
| 8,597,093 B2 | 12/2013 | Engelberg et al. |
| 8,795,138 B1 | 8/2014 | Yeh et al. |
| 8,825,445 B2 | 9/2014 | Hoffman et al. |
| 2001/0020143 A1 | 9/2001 | Stark et al. |
| 2002/0028730 A1 | 3/2002 | Kaufman |
| 2002/0072932 A1 | 6/2002 | Swamy |
| 2002/0082142 A1 | 6/2002 | Cannon et al. |
| 2002/0108000 A1 | 8/2002 | Iori et al. |
| 2002/0128119 A1 | 9/2002 | Arai |

(56) References Cited

U.S. PATENT DOCUMENTS

| | | |
|---|---|---|
| 2002/0142887 A1 | 10/2002 | O'Malley |
| 2002/0156392 A1 | 10/2002 | Arai et al. |
| 2003/0028116 A1 | 2/2003 | Bimbaum |
| 2003/0064860 A1 | 4/2003 | Yamashita et al. |
| 2003/0171188 A1 | 9/2003 | Neil |
| 2003/0171189 A1 | 9/2003 | Kaufman |
| 2003/0211916 A1 | 11/2003 | Capuano |
| 2003/0226695 A1 | 12/2003 | Mault |
| 2004/0058908 A1 | 3/2004 | Keller et al. |
| 2004/0077462 A1 | 4/2004 | Brown et al. |
| 2004/0117214 A1 | 6/2004 | Shea |
| 2005/0010425 A1 | 1/2005 | Chen et al. |
| 2005/0070809 A1 | 3/2005 | Acres |
| 2005/0075214 A1 | 4/2005 | Brown et al. |
| 2005/0083846 A1 | 4/2005 | Bahl |
| 2005/0163346 A1 | 7/2005 | Van Den et al. |
| 2005/0177059 A1 | 8/2005 | Koivumaa et al. |
| 2005/0209002 A1 | 9/2005 | Blythe et al. |
| 2005/0233861 A1 | 10/2005 | Hickman et al. |
| 2005/0272561 A1 | 12/2005 | Cammerata |
| 2006/0020216 A1 | 1/2006 | Oishi et al. |
| 2006/0025282 A1 | 2/2006 | Redmann |
| 2006/0032315 A1 | 2/2006 | Saalastic et al. |
| 2006/0058156 A1 | 3/2006 | Cohen et al. |
| 2006/0094570 A1 | 5/2006 | Schneider |
| 2006/0107822 A1 | 5/2006 | Bowen |
| 2006/0111621 A1 | 5/2006 | Coppi et al. |
| 2006/0111944 A1 | 5/2006 | Sirmans et al. |
| 2006/0113381 A1 | 6/2006 | Hochstein et al. |
| 2006/0240959 A1 | 10/2006 | Huang |
| 2006/0252602 A1 | 11/2006 | Brown et al. |
| 2006/0281976 A1 | 12/2006 | Juang et al. |
| 2006/0288846 A1 | 12/2006 | Logan |
| 2007/0021269 A1 | 1/2007 | Shum |
| 2007/0033068 A1 | 2/2007 | Rao et al. |
| 2007/0033069 A1 | 2/2007 | Rao et al. |
| 2007/0042868 A1 | 2/2007 | Fisher et al. |
| 2007/0060446 A1 | 3/2007 | Asukai et al. |
| 2007/0083092 A1 | 4/2007 | Rippo et al. |
| 2007/0083095 A1 | 4/2007 | Rippo et al. |
| 2007/0113725 A1 | 5/2007 | Oliver et al. |
| 2007/0113726 A1 | 5/2007 | Oliver et al. |
| 2007/0146116 A1 | 6/2007 | Kimbrell |
| 2007/0173377 A1 | 7/2007 | Jamsen et al. |
| 2007/0213608 A1 | 9/2007 | Brown |
| 2007/0219059 A1 | 9/2007 | Schwartz et al. |
| 2007/0249467 A1 | 10/2007 | Hong et al. |
| 2007/0249468 A1 | 10/2007 | Chen |
| 2007/0266065 A1 | 11/2007 | Rosenberg |
| 2007/0271065 A1 | 11/2007 | Gupta et al. |
| 2007/0275825 A1 | 11/2007 | O'Brien |
| 2007/0300185 A1 | 12/2007 | Macbeth et al. |
| 2008/0045384 A1 | 2/2008 | Matsubara et al. |
| 2008/0051919 A1 | 2/2008 | Sakai et al. |
| 2008/0098876 A1 | 5/2008 | Kuo et al. |
| 2008/0103022 A1 | 5/2008 | Dvorak et al. |
| 2008/0110115 A1 | 5/2008 | French |
| 2008/0146890 A1 | 6/2008 | Leboeuf et al. |
| 2008/0146892 A1 | 6/2008 | LeBoeuf et al. |
| 2008/0147502 A1 | 6/2008 | Baker |
| 2008/0153670 A1 | 6/2008 | McKirdy et al. |
| 2008/0162186 A1 | 7/2008 | Jones |
| 2008/0170123 A1 | 7/2008 | Albertson et al. |
| 2008/0176713 A1 | 7/2008 | Olivera et al. |
| 2008/0182723 A1 | 7/2008 | Aaron et al. |
| 2008/0204225 A1 | 8/2008 | Kitchen |
| 2008/0220941 A1 | 9/2008 | Shaw et al. |
| 2008/0262918 A1 | 10/2008 | Wiener |
| 2009/0044687 A1 | 2/2009 | Sorber |
| 2009/0105047 A1 | 4/2009 | Guidi et al. |
| 2009/0131224 A1 | 5/2009 | Yuen |
| 2009/0131759 A1 | 5/2009 | Sims et al. |
| 2009/0138488 A1 | 5/2009 | Shea |
| 2009/0149131 A1 | 6/2009 | Young et al. |
| 2009/0150175 A1 | 6/2009 | Young et al. |
| 2009/0233771 A1 | 9/2009 | Quatrochi et al. |
| 2009/0247366 A1 | 10/2009 | Frumer |
| 2009/0247368 A1 | 10/2009 | Chiang |
| 2009/0258758 A1 | 10/2009 | Hickman et al. |
| 2009/0275442 A1 | 11/2009 | Nissila |
| 2009/0287103 A1 | 11/2009 | Pillai |
| 2009/0292178 A1 | 11/2009 | Ellis et al. |
| 2009/0293298 A1 | 12/2009 | Martorell et al. |
| 2009/0298426 A1 | 12/2009 | Helvick |
| 2010/0017114 A1 | 1/2010 | Tehan et al. |
| 2010/0035726 A1 | 2/2010 | Fisher et al. |
| 2010/0056341 A1 | 3/2010 | Ellis et al. |
| 2010/0099437 A1 | 4/2010 | Moerdijk |
| 2010/0120585 A1 | 5/2010 | Quy |
| 2010/0134257 A1 | 6/2010 | Puleston et al. |
| 2010/0167876 A1 | 7/2010 | Cheng |
| 2010/0185062 A1 | 7/2010 | Salazar et al. |
| 2010/0186078 A1 | 7/2010 | Napoli et al. |
| 2010/0190607 A1 | 7/2010 | Widerman et al. |
| 2010/0216603 A1 | 8/2010 | Somers |
| 2010/0217099 A1 | 8/2010 | LeBoeuf et al. |
| 2010/0222178 A1 | 9/2010 | Shea |
| 2010/0222181 A1 | 9/2010 | Shea |
| 2010/0234699 A1 | 9/2010 | Lanfermann et al. |
| 2010/0273610 A1 | 10/2010 | Johnson |
| 2011/0001827 A1 | 1/2011 | Ortiz et al. |
| 2011/0015039 A1 | 1/2011 | Shea |
| 2011/0015041 A1 | 1/2011 | Shea |
| 2011/0035184 A1 | 2/2011 | Aaron et al. |
| 2011/0059825 A1 | 3/2011 | Mcgown |
| 2011/0098112 A1 | 4/2011 | LeBoeuf et al. |
| 2011/0098583 A1 | 4/2011 | Pandia et al. |
| 2011/0106627 A1 | 5/2011 | LeBoeuf et al. |
| 2011/0137191 A1 | 6/2011 | Kinnunen |
| 2011/0152696 A1 | 6/2011 | Ryan |
| 2011/0165996 A1 | 7/2011 | Paulus et al. |
| 2011/0165998 A1 | 7/2011 | Lav et al. |
| 2011/0179068 A1 | 7/2011 | O'Brien |
| 2011/0195780 A1 | 8/2011 | Lu |
| 2011/0195819 A1 | 8/2011 | Shaw et al. |
| 2011/0205697 A1 | 8/2011 | Callicoat et al. |
| 2011/0212688 A1 | 9/2011 | Griffin et al. |
| 2011/0230142 A1 | 9/2011 | Young et al. |
| 2011/0246908 A1 | 10/2011 | Akram et al. |
| 2011/0263385 A1 | 10/2011 | Shea et al. |
| 2011/0275042 A1 | 11/2011 | Warman et al. |
| 2011/0288381 A1 | 11/2011 | Bartholomew et al. |
| 2011/0319228 A1 | 12/2011 | Shea |
| 2012/0010478 A1 | 1/2012 | Kinnunen et al. |
| 2012/0058859 A1 | 3/2012 | Elsom-Cook et al. |
| 2012/0077580 A1 | 3/2012 | Mahajan et al. |
| 2012/0096249 A1 | 4/2012 | Rubin et al. |
| 2012/0108395 A1 | 5/2012 | Shea |
| 2012/0129138 A1 | 5/2012 | Redmann |
| 2012/0130630 A1 | 5/2012 | Tang et al. |
| 2012/0142429 A1 | 6/2012 | Muller |
| 2012/0178431 A1 | 7/2012 | Gold |
| 2012/0184871 A1 | 7/2012 | Jang et al. |
| 2012/0190502 A1 | 7/2012 | Paulus et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0271143 A1 | 10/2012 | Aragones et al. |
| 2012/0271913 A1 | 10/2012 | Tallgren et al. |
| 2012/0283855 A1* | 11/2012 | Hoffman ................ G01C 21/20 700/91 |
| 2012/0308192 A1 | 12/2012 | Chung et al. |
| 2013/0032634 A1 | 2/2013 | McKirdy |
| 2013/0046477 A1 | 2/2013 | Hyde et al. |
| 2013/0089842 A1 | 4/2013 | Shea |
| 2013/0090213 A1 | 4/2013 | Amini et al. |
| 2013/0090565 A1 | 4/2013 | Quy |
| 2013/0095459 A1 | 4/2013 | Tran |
| 2013/0110265 A1 | 5/2013 | Rahko et al. |
| 2013/0130213 A1 | 5/2013 | Burbank et al. |
| 2013/0155251 A1 | 6/2013 | Moravchik |
| 2013/0178960 A1 | 7/2013 | Sheehan et al. |
| 2013/0217541 A1 | 8/2013 | Shea |
| 2013/0217542 A1 | 8/2013 | Shea |

(56) References Cited

U.S. PATENT DOCUMENTS

| | | | |
|---|---|---|---|
| 2013/0217543 | A1 | 8/2013 | Shea |
| 2013/0218309 | A1 | 8/2013 | Napolitano |
| 2013/0225369 | A1 | 8/2013 | Fisbein et al. |
| 2013/0304377 | A1 | 11/2013 | Hende |
| 2013/0312589 | A1 | 11/2013 | Macpherson |
| 2013/0325326 | A1 | 12/2013 | Blumenberg et al. |
| 2014/0000322 | A1 | 1/2014 | Williams |
| 2014/0013344 | A1 | 1/2014 | Taxier |
| 2014/0089672 | A1 | 3/2014 | Luna et al. |
| 2014/0124570 | A1 | 5/2014 | Franklin |
| 2014/0248996 | A1 | 9/2014 | Adel |
| 2014/0316701 | A1 | 10/2014 | Cardonha et al. |
| 2015/0081210 | A1 | 3/2015 | Yeh et al. |

FOREIGN PATENT DOCUMENTS

| | | | |
|---|---|---|---|
| JP | 2003131785 | A | 5/2003 |
| JP | 2005224318 | | 8/2005 |
| JP | 2007075172 | | 3/2007 |
| JP | 2007322172 | A | 12/2007 |
| JP | 2008242063 | | 10/2008 |
| JP | 2009041964 | A | 2/2009 |
| JP | 2009142333 | | 7/2009 |
| JP | 2009194670 | | 8/2009 |
| JP | 2010088886 | A | 4/2010 |
| JP | 2012108801 | A | 6/2012 |
| JP | 2012189415 | | 10/2012 |
| JP | 2013043061 | | 3/2013 |
| JP | 2013050454 | A | 3/2013 |
| WO | 2009075493 | A2 | 6/2009 |
| WO | 2012070019 | A2 | 5/2012 |
| WO | 2012176193 | | 12/2012 |
| WO | 2013055380 | | 4/2013 |

OTHER PUBLICATIONS

Sabrina Tai-Chen Yeh, David Andrew Young, "Altering Exercise Routes Based on Device Determined Information", file history of related U.S. Appl. No. 14/037,286, filed Sep. 25, 2013.

Sabrina Tai-Chen Yeh, Steven Friedlander, David Andrew Young, "Nonverbal Audio Cues During Physical Activity", file history of related U.S. Appl. No. 14/037,278, filed Sep. 25, 2013.

Sabrina Tai-Chen Yeh, Takashi Hironaka, David Andrew Young, Steven Friedlander, "Quick Login to User Profile on Exercise Machine", file history of related U.S. Appl. No. 14/037,263, filed Sep. 25, 2013.

Sabrina Tai-Chen Yeh, David Andrew Young, Steven Friedlander, "Determine Exercise Routes Based on Device Determined Information", file history of related U.S. Appl. No. 14/037,276, filed Sep. 25, 2013.

Sabrina Ta-Chen Yeh, Steven Friedlander, David Andrew Young, "Synchronized Exercise Buddy Headphones", file history of related U.S. Appl. No. 14/037,267, filed Sep. 25, 2013.

Sabrina Tai-Chen Yeh, David Andrew Young, Takashi Hironaka, Steven Friedlander, "Presenting Audio Based on Biometrics Parameters", file history of related U.S. Appl. No. 14/037,271, filed Sep. 25, 2013.

Sabrina Tai-Chen Yeh, Steven Friedlander, David Andrew Young, "Presenting Audio Video on Biometrics Parameters", file history of related U.S. Appl. No. 14/037,252, filed Sep. 25, 2013.

Sabrina Tai-Chen Yeh, Jenny Therese Fredriksson, "Combining Data Sources to Provide Accurate Effort Monitoring", file history of related U.S. Appl. No. 14/037,224, filed Sep. 25, 2013.

Sabrina Tai-Chen Yeh, Jenny Therese Fredriksson, "Intelligent Device Mode Shifting Based on Activity", file history of related U.S. Appl. No. 14/037,228, filed Sep. 25, 2013.

Sabrina Tai-Chen Yeh, David Andrew Young, Steven Friedlander, Determining Exercise Routes Based on Device Determined Information, related U.S. Appl. No. 14/037,276. Non-Final Office Action dated Mar. 31, 2015.

Sabrina Tai-Chen Yeh, David Andrew Young, Steven Firedlander, Determining Exercise Routes Based on Device Determined Information, related U.S. Appl. No. 14/037,276, Applicant's response to Non-Final Office Action filed Apr. 1, 2015.

Julia Anne Framel, Aravind Babu Asam, Guru Prashanth Balasubramanian, "User Device Position Indication for Security and Distributed Race Challenges", related U.S. Appl. No. 14/261,075, Applicant's response to Non-Final Office Action filed Mar. 30, 2015.

Sabrina Tai-Chen Yeh; Tai Ashi Hironaka, David Andrew Young, Steven Friedlander, "Quick Login to User Profile on Exercise Machine", related U.S. Appl. No. 14/037,263, Non-Final Office Action dated May 27, 2015.

Sabrina Tai-Chen Yeh, Takashi Hironaka, David Andrew Young, Steven Friedlander, "Quick Login to User Profile on Exercise Machine", related U.S. Appl. No. 14/037,263, Applicant's response to Non-Final Office Action filed May 29, 2015.

Julie Anne Framel, Aravind Babu Asam, Guru Prashanth Balasubramanian, Takeshi Suzuki, Charles D. Hedrick Jr.; "User Device Position Indication for Security and Distributed Race Challenges" related U.S. Appl. No. 13/644,044 non-final office action dated Apr. 14, 2014.

Julie Anne Framel, Aravind Babu Asam, Guru Prashanth Balasubramanian, Takeshi Suzuki, Charles D. Hedrick Jr.; "User Device Position Indication for Security and Distributed Race Challenges" related U.S. Appl. No. 13/644,044 applicants response to non-final office action filed Apr. 24, 2014.

Sabrina Tai-Chen Yeh, Steven Friedlander, David Andrew Young, "Presenting Audio Based on Biometrics Parameters", related U.S. Appl. No. 14/037,252, Non-Final Office Action dated Aug. 4, 2015.

Julia Anne Framel, Aravind Babu Asam, Guru Prashanth Balasubramanian, Takeshi Suzuki, Charles D. Hedrick, "User Device Position Indication for Security and Distributed Race Challenges", related U.S. Appl. No. 14/261,075, Non-Final Office Action dated Mar. 23, 2015.

Sabrina Tai-Chen Yeh, Jenny Therese Fredriksson, "Combining Data Sources to Provide Accurate Effort Monitoring" related U.S. Appl. No. 14/255,663 non-final office action dated Sep. 12, 2014.

Sabrina Tai-Chen Yeh, Jenny Therese Fredriksson, "Combining Data Sources to Provide Accurate Effort Monitoring" related U.S. Appl. No. 14/255,663 applicants response to the non-final office action filed Oct. 30, 2014.

Sabrina Tai-Chen Yeh, David Andrew Young, Steven Firedlander, "Determining Exercise Routes Based on Device Determined Information", related U.S. Appl. No. 14/037,276, Final Office Action dated Jun. 15, 2015.

Sabrina Tai-Chen Yeh, David Andrew Young, Steven Firedlander, "Determining Exercise Routes Based on Device Determined Information", related U.S. Appl. No. 14/037,276, Applicant's response to Final Office Action filed Jun. 17, 2015.

Judith A. Markowitz, "Voice Biometrics, Who Are You? Your voice along can be used to verify your personal identity -unobtrusively and invisibly." Sep. 2000/ vol. 43. No. 9, Communications of the ACM. http://www.web2.utc.edu/~djy471/documents/voice-biometrics-p66-markowitz.pdf.

Veli-Jussi Raitila, "Tag, you're it—NFC in a home environment" TKK T-110.5190 Seminar on Internertworking, Finland, pp. 1-6, 2007. http://www.tml.tkk.fi/Publications/C/23/papers/Raitila_final.pdf.

Performtek Sensor Technology, "PerformTek Technology, Monitor Fitness Metrics Using Earbud Sensor Technology" http://www.valencell.com/preformtek-sensor-technology, website printed Sep. 17, 2013.

Steve Silverman, "Biometic Exercises" http://www.livestrong.com/article/282962-biometrics-exercises/, Mar. 31, 2011.

Sabrina Tai-Chen Yeh, David Andrew Young, Takashi Hironaka, Steven Friedlander, "Nonverbal Audio Cues During Physical Activity", related U.S. Appl. No. 14/037,271, Non-Final Office Action dated Jul. 2, 2015.

Sabrina Tai-Chen Yeh, David Andrew Young, Takashi Hironaka, Steven Friedlander, "Nonverbal Audio Cues During Physical Activity", related U.S. Appl. No. 14/037,271, Applicant's response to Non-Final Office Action filed Jul. 13, 2015.

(56) References Cited

OTHER PUBLICATIONS

Sabrina Tai-Chen Yeh, David Andrew Young, "Altering Exercise Based on Device Determined Information", related U.S. Appl. No. 14/037,286, Non-Final Office Action dated Aug. 28, 2015.

Sabrina Tai-Chen Yeh, David Andrew Young, "Altering Exercise Based on Device Determined Information", related U.S. Appl. No. 14/037,286, Applicant's response to Non-Final Office Action filed Sep. 8, 2015.

Sabrina Tai-Chen Yeh, David Andrew Young, Steven Friedlander, "Quick Login to User Profile on Exercise Machine", related U.S. Appl. No. 14/037,263, Final Office Action dated Aug. 20, 2015.

Sabrina Tai-Chen Yeh, David Andrew Young, Steven Friedlander, "Quick Login to User Profile on Exercise Machine", related U.S. Appl. No. 14/037,263, Applicant's response to Final Office Action filed Aug. 25, 2015.

Sabrina Tai-Chen Yeh, Jenny Therese Fredriksson, "Combining Data Sources to Provide Accurate Effort Monitoring", related U.S. Appl. No. 14/255,663, Final Office Action dated Oct. 2, 2015.

Sabrina Tai-Chen Yeh, Jenny Therese Fredriksson, "Combining Data Sources to Provide Accurate Effort Monitoring", related U.S. Appl. No. 14/255,663, Applicant's response to Final Office Action filed Oct. 2, 2015.

Sabrina Tai-Chen Yeh, Steven Friedlander, David Andrew Young, "Nonverbal Audio Cues During Physical Activity", related U.S. Appl. No. 14/037,278 non-final office action dated Oct. 22, 2015.

Sabrina Tai-Chen Yeh, Steven Friedlander, David Andrew Young, "Nonverbal Audio Cues During Physical Activity", related U.S. Appl. No. 14/037,278 applicants response to non-final office action filed Oct. 23, 2015.

Sabrina Tai-Chen Yeh, Jenny Therese Frediksson, "Intelligent Device Mode Shifting Based on Activity", related U.S. Appl. No. 14/037,228 non-final office action date Oct. 26, 2015.

Sabrina Tai-Chen Yeh, Jenny Therese Frediksson, "Intelligent Device Mode Shifting Based on Activity", related U.S. Appl. No. 14/037,228 applicants response to non-final office action filed Oct. 27, 2015.

Sabrina Tai-Chen Yeh, Takashi Hironaka, David Andrew Young, Steven Friedlander, "Quick Login to User Profile on Exercise Machine", related U.S. Appl. No. 14/037,263, Non-Final Office Action dated Nov. 3, 2015.

Sabrina Tai-Chen Yeh, Takashi Hironaka, David Andrew Young, Steven Friedlander, "Quick Login to User Profile on Exercise Machine", related U.S. Appl. No. 14/037,263, Applicant's response to Non-Final Office Action filed Nov. 4, 2015.

Sabrina Tai-Chen Yeh, David Andrew Young, "Altering Exercise Based on Device Determined Information", related U.S. Appl. No. 14/037,286, Final Office Action dated Dec. 3, 2015.

Sabrina Tai-Chen Yeh, David Andrew Young, Takashi Hironaka, Steven Firedlander, "Presenting Audio Based on Biometrics Parameters", related U.S. Appl. No. 14/037,271, Applicant's responese to Non-Final Office Action filed Nov. 25, 2015.

Sabrina Tai-Chen Yeh, David Andrew Young, Takashi Hironaka, Steven Friedlander, "Presenting Audio Based on Biometrics Parameters", related U.S. Appl. No. 14/037,271, Final Office Action dated Nov. 24, 2015.

Sabrina Tai-Chen Yeh, David Andrew Young, "Altering Exercise Routes Based on Device Determined Information", related U.S. Appl. No. 14/037,286. Applicant's response to Final Office Action filed Dec. 8, 2015.

* cited by examiner

DEVICES AND METHODS FOR HEALTH TRACKING AND PROVIDING INFORMATION FOR IMPROVING HEALTH

I. FIELD OF THE INVENTION

The present application relates generally to digital ecosystems that are configured for use to track a user's health-related biometrics.

II. BACKGROUND OF THE INVENTION

Society is becoming increasingly health-conscious. However, there are currently no adequately robust tools for providing diagnostics and recommendations for improving one's health and fitness.

SUMMARY OF THE INVENTION

Accordingly, present principles recognize that a variety of health monitoring devices and/or sensors may be used to help a user improve their health and fitness by e.g. performing calculations for reaching health targets, providing exercise goals, and providing interactive functions making reaching such goals more enjoyable.

Thus, in a first aspect a device includes at least one computer readable storage medium bearing instructions executable by a processor, and at least one processor configured for accessing the computer readable storage medium to execute the instructions to configure the processor for receiving input pertaining to at least a first health parameter, monitoring at least one biometric of a user, and determining whether the user's biometric conforms to the first health parameter. The instructions also configure the processor for providing an indication that the biometric conforms to the first health parameter and providing information pertaining to a reference biometric in response to determining that the user's biometric conforms to the first health parameter, and providing a recommendation for conforming to the first health parameter in response to determining that the user's biometric does not conform to the first health parameter. The reference biometric is of the same biometric type as the user's biometric.

The user's biometric may be monitored at least in part based on signals from one or more biometric sensors configured to gather biometric information from the user. In some embodiments, the input pertaining to the first health parameter may be received from the user.

Also in some embodiments, the information pertaining to the reference biometric may include the reference biometric. The reference biometric may be derived by the device from information from a public health agency website and/or from a government website. Furthermore, the reference biometric may be a biometric average of plural persons of the same age and gender as the user.

If desired, determining whether the user's biometric conforms to the first health parameter may include comparing the user's biometric against the first health parameter and determining whether the user's biometric is within a threshold of the first health parameter.

Also if desired, the indication and/or recommendation may be provided on a user interface (UI) that may be presented on different device than the device executing the instructions. The UI may include a link to a website pertaining to health information. The recommendation may include an instruction for the user to alter the user's physical activity in at least one respect, and/or may include an indication of sustenance to consume. In some embodiments, the biometric type may be one of blood oxygen level, glucose level, sodium level, and resting heart rate.

In another aspect, a method includes receiving a biometric target from a person, receiving at least one signal from a biometric sensor sensing a biometric of the person, determining whether the biometric target has been reached based at least in part on the signal, and providing at least a first indication that the biometric target has not been reached responsive to a determination that the biometric target has not been reached.

In still another aspect, a device includes at least one computer readable storage medium bearing instructions executable by a processor, and at least one processor configured for accessing the computer readable storage medium to execute the instructions to configure the processor for receiving at least one physical fitness target from a user, determining at least one biometric range for which at least one biometric of the user is to reach to conform to the physical fitness target, and providing a fitness plan to the user to reach the physical fitness target.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
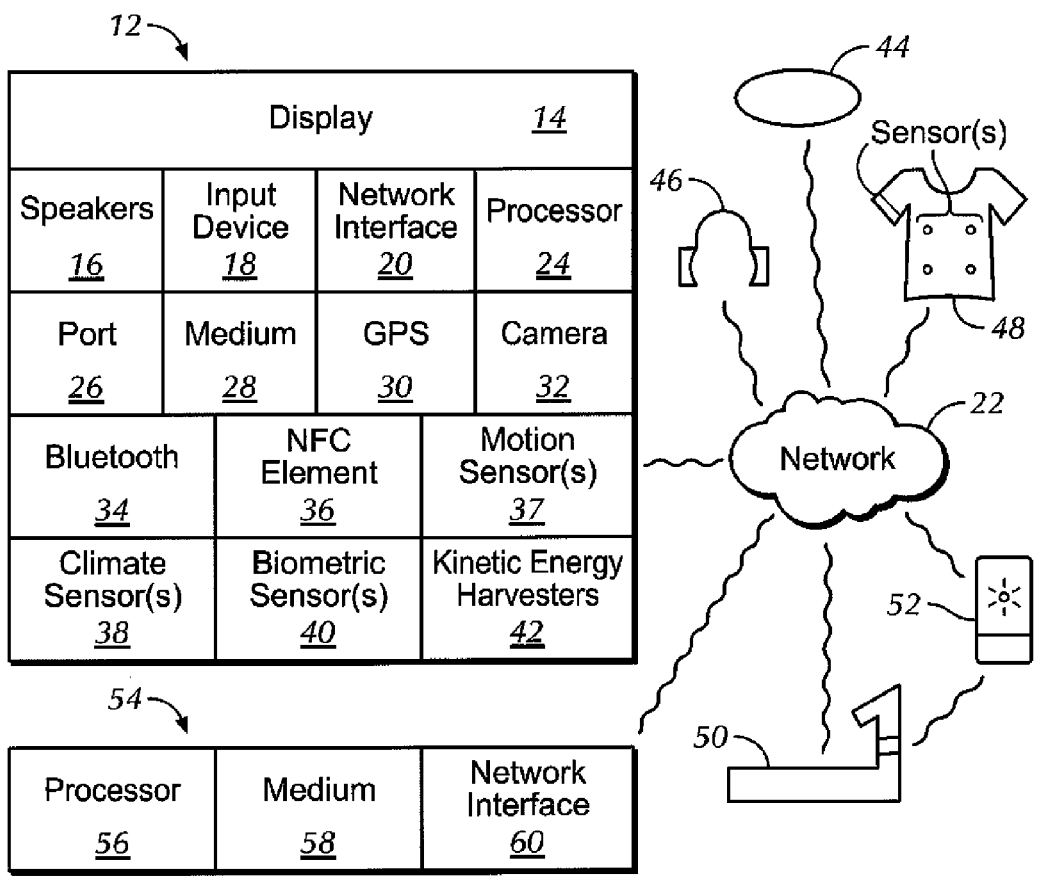
FIG. 1 is a block diagram of an example system including an example CE device in accordance with present principles.

This disclosure relates generally to consumer electronics (CE) device based user information. With respect to any computer systems discussed herein, a system may include server and client components, connected over a network such that data may be exchanged between the client and server components. The client components may include one or more computing devices including televisions (e.g. smart TVs, Internet-enabled TVs), computers such as laptops and tablet computers, and mobile devices including smart phones and additional examples discussed below. These client devices may employ, as non-limiting examples, operating systems from Apple, Google, or Microsoft. A Unix operating system may be used. These operating systems can execute one or more browsers such as a browser made by Microsoft or Google or Mozilla or other browser program that can access web applications hosted by the Internet servers over a network such as the Internet, a local intranet, or a virtual private network.

As used herein, instructions refer to computer-implemented steps for processing information in the system. Instructions can be implemented in software, firmware or hardware; hence, illustrative components, blocks, modules, circuits, and steps are set forth in terms of their functionality.

A processor may be any conventional general purpose single- or multi-chip processor that can execute logic by means of various lines such as address lines, data lines, and control lines and registers and shift registers. Moreover, any logical blocks, modules, and circuits described herein can be implemented or performed, in addition to a general purpose processor, in or by a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can be implemented by a controller or state machine or a combination of computing devices.

Any software and/or applications described by way of flow charts and/or user interfaces herein can include various subroutines, procedures, etc. It is to be understood that logic divulged as being executed by e.g. a module can be redistributed to other software modules and/or combined together in a single module and/or made available in a shareable library.

Logic when implemented in software, can be written in an appropriate language such as but not limited to C# or C++, and can be stored on or transmitted through a computer-readable storage medium such as a random access memory (RAM), read-only memory (ROM), electrically erasable programmable read-only memory (EEPROM), compact disk read-only memory (CD-ROM) or other optical disk storage such as digital versatile disc (DVD), magnetic disk storage or other magnetic storage devices including removable thumb drives, etc. A connection may establish a computer-readable medium. Such connections can include, as examples, hard-wired cables including fiber optics and coaxial wires and twisted pair wires. Such connections may include wireless communication connections including infrared and radio.

In an example, a processor can access information over its input lines from data storage, such as the computer readable storage medium, and/or the processor accesses information wirelessly from an Internet server by activating a wireless transceiver to send and receive data. Data typically is converted from analog signals to digital by circuitry between the antenna and the registers of the processor when being received and from digital to analog when being transmitted. The processor then processes the data through its shift registers to output calculated data on output lines, for presentation of the calculated data on the CE device.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

Before describing FIG. 1, it is to be understood that the CE devices and software described herein are understood to be usable in the context of a digital ecosystem. Thus, as understood herein, a computer ecosystem, or digital ecosystem, may be an adaptive and distributed socio-technical system that is characterized by its sustainability, self-organization, and scalability. Inspired by environmental ecosystems, which consist of biotic and abiotic components that interact through nutrient cycles and energy flows, complete computer ecosystems consist of hardware, software, and services that in some cases may be provided by one company, such as Sony Electronics. The goal of each computer ecosystem is to provide consumers with everything that may be desired, at least in part services and/or software that may be exchanged via the Internet. Moreover, interconnectedness and sharing among elements of an ecosystem, such as applications within a computing cloud, provides consumers with increased capability to organize and access data and presents itself as the future characteristic of efficient integrative ecosystems.

Two general types of computer ecosystems exist: vertical and horizontal computer ecosystems. In the vertical approach, virtually all aspects of the ecosystem are associated with the same company (e.g. produced by the same manufacturer), and are specifically designed to seamlessly interact with one another. Horizontal ecosystems, one the other hand, integrate aspects such as hardware and software that are created by differing entities into one unified ecosystem. The horizontal approach allows for greater variety of input from consumers and manufactures, increasing the capacity for novel innovations and adaptations to changing demands. But regardless, it is to be understood that some digital ecosystems, including those referenced herein, may embody characteristics of both the horizontal and vertical ecosystems described above.

Accordingly, it is to be further understood that these ecosystems may be used while engaged in physical activity to e.g. provide inspiration, goal fulfillment and/or achievement, automated coaching/training, health and exercise analysis, convenient access to data, group sharing (e.g. of fitness data), and increased accuracy of health monitoring, all while doing so in a stylish and entertaining manner. Further still, the devices disclosed herein are understood to be capable of making diagnostic determinations based on data from various sensors (such as those described below in reference to FIG. 1) for use while exercising, for exercise monitoring (e.g. in real time), and/or for sharing of data with friends (e.g. using a social networking service) even when not all people have the same types and combinations of sensors on their respective CE devices.

Now specifically referring to FIG. 1, an example system 10 is shown, which may include one or more of the example devices mentioned above and described further below to enhance fitness and/or health experiences in accordance with present principles. The first of the example devices included in the system 10 is an example consumer electronics (CE) device 12 that may be waterproof (e.g., for use while swimming). The CE device 12 may be, e.g., a computerized Internet enabled ("smart") telephone, a tablet computer, a notebook computer, a wearable computerized device such as e.g. computerized Internet-enabled watch, a computerized Internet-enabled bracelet, other computerized Internet-enabled fitness devices, a computerized Internet-enabled music player, computerized Internet-enabled head phones, a computerized Internet-enabled implantable device such as an implantable skin device, etc., and even e.g. a computerized Internet-enabled television (TV). Regardless, it is to be understood that the CE device 12 is configured to undertake present principles (e.g. communicate with other devices to undertake present principles, execute the logic described herein, and perform any other functions and/or operations described herein).

Accordingly, to undertake such principles the CE device 12 can include some or all of the components shown in FIG. 1. For example, the CE device 12 can include one or more touch-enabled displays 14, one or more speakers 16 for outputting audio in accordance with present principles (e.g. an alarm), and at least one additional input device 18 such as e.g. an audio receiver/microphone for e.g. entering audible commands to the CE device 12 to control the CE device 12. The example CE device 12 may also include one or more network interfaces 20 for communication over at least one network 22 such as the Internet, an WAN, an LAN, etc. under control of one or more processors 24. It is to be understood that the processor 24 controls the CE device 12 to undertake present principles, including the other elements of the CE device 12 described herein such as e.g. controlling the display 14 to present images thereon and receiving input therefrom. Furthermore, note the network interface 20 may be, e.g., a wired or wireless modem or router, or other appropriate interface such as, e.g., a wireless telephony transceiver, WiFi transceiver, etc.

In addition to the foregoing, the CE device 12 may also include one or more input ports 26 such as, e.g., a USB port to physically connect (e.g. using a wired connection) to another CE device and/or a headphone port to connect headphones to the CE device 12 for presentation of audio from the CE device 12 to a user through the headphones. The CE device 12 may further include one or more tangible computer readable storage mediums 28 such as disk-based or solid state storage, it being understood that the computer readable storage medium 28 may not be a carrier wave. Also in some embodiments, the CE device 12 can include a position or location receiver such as but not limited to a GPS receiver and/or altimeter 30 that is configured to e.g. receive geographic position information from at least one satellite and provide the information to the processor 24 and/or determine an altitude at which the CE device 12 is disposed in conjunction with the processor 24. However, it is to be understood that that another suitable position receiver other than a GPS receiver and/or altimeter may be used in accordance with present principles to e.g. determine the location of the CE device 12 in e.g. all three dimensions.

Continuing the description of the CE device 12, in some embodiments the CE device 12 may include one or more cameras 32 that may be, e.g., a thermal imaging camera, a digital camera such as a webcam, and/or a camera integrated into the CE device 12 and controllable by the processor 24 to gather pictures/images and/or video in accordance with present principles. Also included on the CE device 12 may be a Bluetooth transceiver 34 and other Near Field Communication (NFC) element 36 for communication with other devices using Bluetooth and/or NFC technology, respectively. An example NFC element can be a radio frequency identification (RFID) element.

Further still, the CE device 12 may include one or more motion sensors 37 (e.g., an accelerometer, gyroscope, cyclometer, magnetic sensor, infrared (IR) motion sensors such as passive IR sensors, an optical sensor, a speed and/or cadence sensor, a gesture sensor (e.g. for sensing gesture command), etc.) providing input to the processor 24. The CE device 12 may include still other sensors such as e.g. one or more climate sensors 38 (e.g. barometers, humidity sensors, wind sensors, light sensors, temperature sensors, etc.) and/or one or more biometric sensors 40 (e.g. heart rate sensors and/or heart monitors, calorie counters, blood pressure sensors, perspiration sensors, odor and/or scent detectors, fingerprint sensors, facial recognition sensors, iris and/or retina detectors, DNA sensors, oxygen sensors (e.g. blood oxygen sensors and/or VO2 max sensors), glucose and/or blood sugar sensors, blood oxygen sensors, other oxygen sensors, sodium sensors, sleep sensors (e.g. a sleep tracker), pedometers and/or speed sensors, body temperature sensors, nutrient and metabolic rate sensors, voice sensors, lung input/output and other cardiovascular sensors, mood sensors, and still other sensors for providing biometrics of the biometric types discussed herein, etc.) also providing input to the processor 24. In addition to the foregoing, it is noted that in some embodiments the CE device 12 may also include a kinetic energy harvester 42 to e.g. charge a battery (not shown) powering the CE device 12.

Still referring to FIG. 1, in addition to the CE device 12, the system 10 may include one or more other CE device types such as, but not limited to, a computerized Internet-enabled bracelet 44, computerized Internet-enabled headphones and/or ear buds 46, computerized Internet-enabled clothing 48, a computerized Internet-enabled exercise machine 50 (e.g. a treadmill, exercise bike, elliptical machine, etc.), etc. Also shown is a computerized Internet-enabled gymnasium entry kiosk 52 permitting authorized entry to a gymnasium housing the exercise machine 50. It is to be understood that other CE devices included in the system 10 including those described in this paragraph may respectively include some or all of the various components described above in reference to the CE device 12 such but not limited to e.g. the biometric sensors and motion sensors described above, as well as the position receivers, cameras, input devices, and speakers also described above.

Thus, for instance, the headphones/ear buds 46 may include a heart rate sensor configured to sense a person's heart rate when a person is wearing the head phones, the clothing 48 may include sensors such as perspiration sensors, climate sensors, and heart sensors for measuring the intensity of a person's workout, the exercise machine 50 may include a camera mounted on a portion thereof for gathering facial images of a user so that the machine 50 may thereby determine whether a particular facial expression is indicative of a user struggling to keep the pace set by the exercise machine 50 and/or an NFC element to e.g. pair the machine 50 with the CE device 12 and hence access a database of preset workout routines, and the kiosk 52 may include an NFC element permitting entry to a person authenticated as being authorized for entry based on input received from a complimentary NFC element (such as e.g. the NFC element 36 on the device 12). Also note that all of the devices described in reference to FIG. 1, including a server 54 to be described shortly, may communicate with each other over the network 22 using a respective network interface included thereon, and may each also include a computer readable storage medium that may not be a carrier wave for storing logic and/or software code in accordance with present principles.

Now in reference to the afore-mentioned at least one server 54, it includes at least one processor 56, at least one tangible computer readable storage medium 58 that may not be a carrier wave such as disk-based or solid state storage, and at least one network interface 60 that, under control of the processor 56, allows for communication with the other CE devices of FIG. 1 over the network 22, and indeed may facilitate communication therebetween in accordance with present principles. Note that the network interface 60 may be, e.g., a wired or wireless modem or router, WiFi transceiver, or other appropriate interface such as, e.g., a wireless telephony transceiver.

Accordingly, in some embodiments the server 54 may be an Internet server, may facilitate fitness coordination and/or data exchange between CE device devices in accordance with present principles, provide information to one or more CE devices in accordance with present principles, and may include and perform "cloud" functions such that the CE devices of the system 10 may access a "cloud" environment via the server 54 in example embodiments to e.g. access a fitness plan in accordance with present principles and/or stream music to listen to while exercising.

Figure 2:
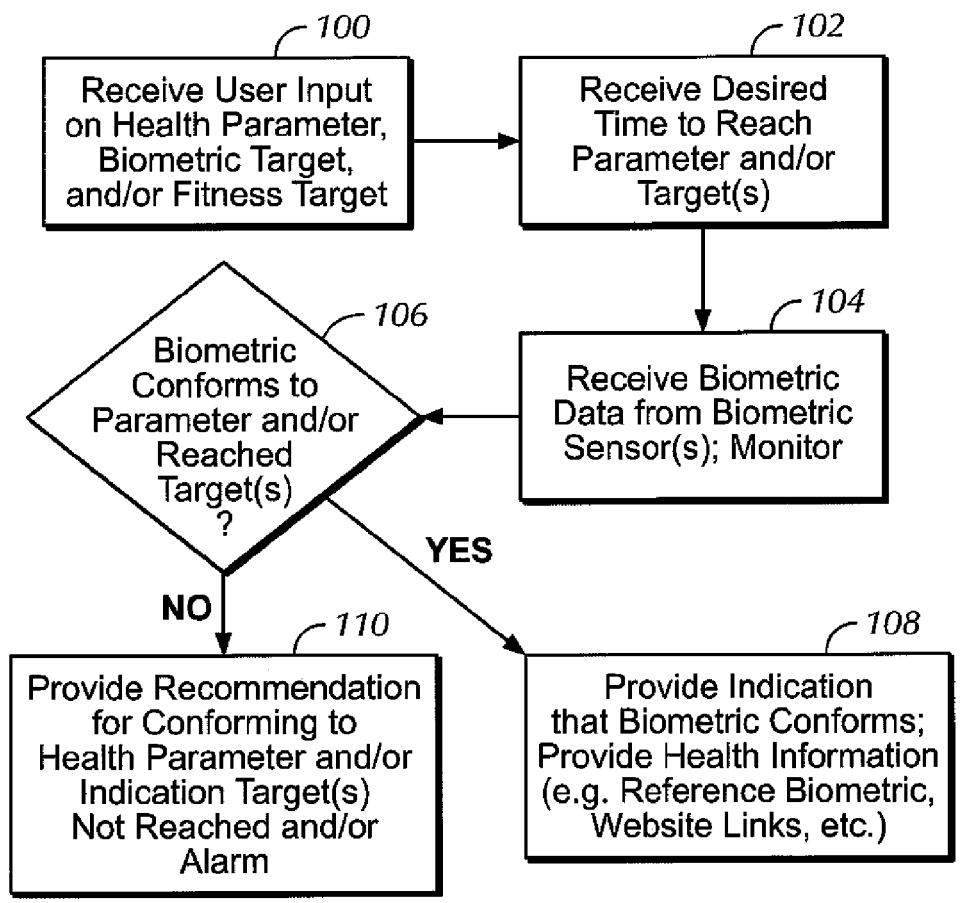
FIGS. 2 and 3 are example flowcharts of logic to be executed by a CE device in accordance with present principles.

Turning now to FIG. 2, an example flowchart of logic to be executed by a CE device, such as the CE device 12, in accordance with present principles. Beginning at block 100, the logic receives user input pertaining to at least one health parameter, biometric target, and/or physical fitness target. For instance, at block 100 the logic may receive from a user respective e.g. biometric parameters and/or biometric targets in the form of numerical values for one or more biometric parameter types for which the user aspires to have the user's body conform. E.g., a user may input e.g. an "ideal" body temperature, blood pressure, sodium level, etc. Further still, e.g. a fitness target may be a particular body mass index (BMI) value for which the user aspires to have the user's body conform, or another health-associated target that e.g. does not directly correspond to an output from a biometric sensor but may nonetheless be derived therefrom at the device of FIG. 2 by computing and/or deriving information from sensor output.

For instance, a BMI indication may not necessarily directly correspond to the output of a biometric sensor, but can be derived from outputs by e.g. dividing the user's weight by the square of the user's height. Thus, the user's weight (e.g. and even height) may be provided by a biometric sensor such as a weight sensor (e.g. a scale), but the computation itself to derive the user's BMI by dividing the user's weight by the square of the user's height may be undertaken by the device undertaking the logic of FIG. 2 based on the weight output received from the weight sensor.

In any case, after block 100 the logic proceeds to block 102 where the logic receives a (e.g. desired) time in which the user is to and/or wishes to reach the parameter(s) and/or target(s). The time may be subsequently used to e.g. present an alarm at the time responsive to the parameter and/or target not being reached by the time (e.g. at or within one month) in accordance with present principles. In any case, after block 102 the logic proceeds to block 104 where the logic receives at least one signal from a biometric sensor sensing a biometric of the user in accordance with present principles. E.g., input may be received from a smart wrist band including plural biometric sensors of different types and provided to another device such as e.g. a smart phone of the user. Additionally or alternatively at block 104, the logic monitors the user's biometrics (by e.g. generating and updating a history of received biometric information, and/or processing and/or analyzing received biometric information) for making determinations as described herein based on the received data.

Regardless, after block 104 the logic proceeds to decision diamond 106, where the logic determines whether the biometric information that has been received conforms to the parameters and/or has reached the target(s). The logic may do so by e.g. comparing biometric data associated with the user from the biometric sensor(s) against the first health parameter to determine whether the user's biometric is within a threshold of the first health parameter. Thus, for instance, the logic may e.g. every tenth of a second determine if the parameter and/or target has been reached based on e.g. comparing most-recently received biometric information to the parameter and/or target and determining whether it is within a threshold of the target. Note that parameters and targets in accordance with present principles may be a specific number and/or value, and/or may be a number and/or value range such that e.g. a target range for healthy sodium levels in a person's body may be determined to have or have not been reached at block 106.

Thus, an affirmative determination at diamond 106 causes the logic to move to block 108 where the logic provides an indication (e.g. on a user interface (UI)) that the user's biometric(s) conforms to the parameter(s) and/or target(s). Also at block 108, the logic may provide (e.g. health and fitness) information on the UI such as e.g. a reference biometric as will be discussed further below, links to health websites and/or health information, etc. Note that the indication e.g. as provided on a UI may be presented on the device providing the biometric information such as e.g. a smart bracelet, and/or may be provided on another device in communication with the device providing the biometric information such as e.g. a smart phone of the user.

Still in reference to diamond 106, should a negative determination be made thereat, the logic instead proceeds to block 110 where the logic provides a recommendation for conforming to the first health parameter and/or an indication that target(s) has not been reached. The recommendation and/or indication that the target(s) has not been reached may be presented on a UI in accordance with present principles, where the UI may be presented on the device providing the biometric information such as e.g. a smart bracelet, and/or may be presented on another device in communication with the device providing the biometric information such as e.g. a smart phone of the user.

The UI presented at block 110 may include e.g. health and fitness information, one or more reference biometrics, links to health websites and/or health information, one or more instructions for the user to alter the user's physical activity and/or behavior in at least one respect to conform to the parameter and/or reach the target (e.g. engage in, and/or refrain from, a particular activity), one or more instructions for the user to alter the user's eating habits in at least one respect to conform to the parameter and/or reach the target (e.g. consume certain foods or drink, and/or refrain from consuming certain foods or drink), etc.

Referring back to the reference biometric from above, a reference biometric in accordance with present principles may be e.g. a particular number, parameter, statistic, average, etc. for the biometric type of the respective user biometric that is commonly accepted (e.g. within the medical community) as being healthy, a "healthy normal," and/or within a normal range as indicated at e.g. a health website providing such information and that is accessed by the device undertaking the logic of FIG. 2, and hence a reference biometric need not necessarily be associated with the user per se and/or specifically pertain to the user. Thus, in some embodiments the reference biometric may be derived from information from a public health website and/or government website (e.g. the U.S. Surgeon General's website, the Food and Drug Administration website, etc.). Furthermore, owing to e.g. a "healthy" reference biometric sometimes varying depending on a person's age, fitness, body mass index (BMI), gender, etc., note that a reference biometric in accordance with present principles may be determined, accessed and/or derived by the device undertaking the logic of FIG. 2 based on e.g. the user's age and gender, or other factors discussed herein. As an example, a reference biometric in accordance with present principles may be a biometric average for a "healthy" blood glucose level of plural persons of the same age and gender as the user.

Figure 3:
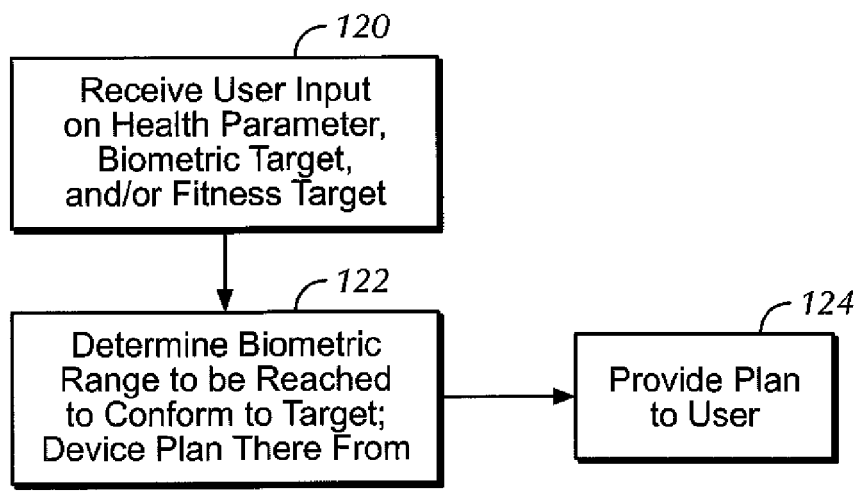

Now in reference to FIG. 3, another exemplary flow chart of logic to be executed by a CE device in accordance with present principles is shown. Note that the logic of FIG. 3 may be combined with the logic of FIG. 2 (e.g. continuing after block 110) and/or may be executed in isolation from FIG. 2. In any case, the logic of FIG. 3 begins at block 120 where the logic, e.g. receives at least one health parameter and/or target from a user as described in reference to block 100 (e.g. if not already done so at block 100 in conjunction with the logic of FIG. 3).

After receiving at least one physical fitness target from a user such at block 100 and/or block 120, the logic determines at block 122 at least one biometric range for which one or more biometrics of the user is to reach to conform to the user's fitness target. The fitness target may be, e.g. a desired BMI, a desired blood oxygen level, a desired oxygen consumption amount, a desired blood glucose level, a desired blood sodium level, a desired (e.g. resting) heart rate, a desired blood pressure, a desired core body temperature, a desired ratio of calorie intake to calorie usage, etc.

Also at block 122, the logic derives and/or determines a fitness plan, routine, outline, fitness program, and/or scheme in accordance with present principles for undertaking actions and/or refraining from actions to progress toward conforming to the desired parameter and/or target. Thus, e.g., the fitness plan may be e.g. one or more (e.g. a set) of activities to regularly perform and/or perform at intervals (e.g. workout routines (e.g. and times) to engage in with the plan indicating details e.g. workout by workout (and/or day by day) for a total number of workouts, diets and/or meal plans providing detailed information meal by meal for a total number of meals, etc.). The information indicated in the plan may be determined based on e.g. accessing a data table correlating exercises and/or dieting with one or more biometric types for thus improving biometrics of the biometric types, which may then be incorporated into the plan by the device and provided to the user.

In addition to or in lieu of the foregoing, the fitness plan may be e.g. an indication of the total time a particular activity or activities are to be undertaken to reach the user's physical fitness target. Such a time may be determined by e.g. accessing an average (e.g. reference) time (e.g. stored at a server with which the device undertaking the logic of FIG. 3 can communicate) to incrementally alter the biometric type of one or more biometrics when undertaking a particular activity. The average time may be e.g. a generally-accepted average time within the medical community, may be an average of actual times of people other than the user, may be a reference time as provided by a nutritionist and/or physician, etc.

Regardless, after accessing such information, the logic may determine a number of increments (e.g. based on the same particular and/or specific increment (e.g. a increment value or constant) for the average time to incrementally alter the biometric type as set forth immediately above) the particular biometric of the user is from the biometric range/target and hence the time to reach the target by taking e.g. a current biometric for the user and/or most recent biometric sensor output for the biometric and e.g. subtracting it from the targeted biometric to arrive at a first number. The first number is then divided by the e.g. specific increment value/constant for the average time to incrementally alter the biometric type (as discussed above) to thus determine a second number that is the number of increments from which the user's biometric is from the biometric target. Time to reach the target may then be calculated by multiplying the second number by the average time to incrementally alter the biometric type. In some embodiments, one or both of the number of increments away and/or the time to reach the target may be presented to the user on one of the Ws discussed herein and/or as part of a fitness plan in accordance with present principles.

Figure 4:
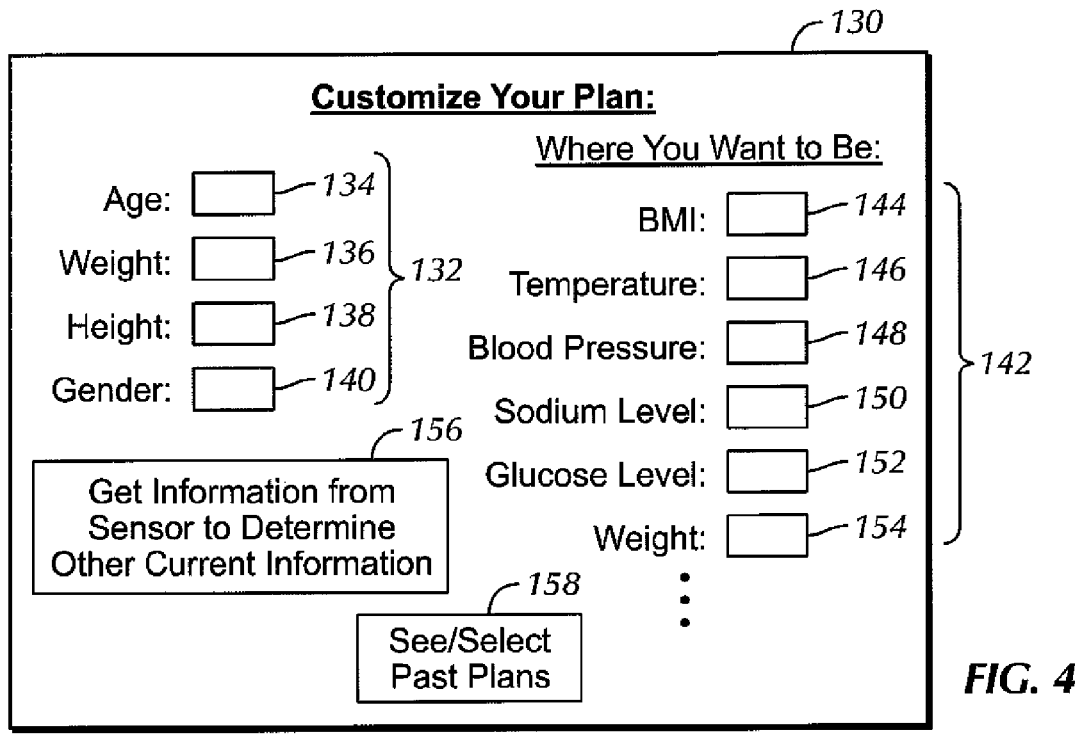
FIGS. 4-6 are example user interfaces (UIs) presentable on a CE device in accordance with present principles.

Continuing the detailed description in reference to FIG. 4, an exemplary UI is shown that is presentable on a CE device in accordance with present principles for e.g. inputting user information for the CE device to determine a fitness plan. The UI 130 thus includes a first column 132 for inputting one or more (e.g. current) biometrics or other user information into respective input entry boxes, including an age input box 134 for inputting the user's age, a weight input box 136 for inputting the user's weight, a height input box 138 for inputting the user's height, and gender input box 140 for inputting the user's gender. A second column 142 is shown for inputting one or more targets for respective biometric types into respective input entry boxes, including e.g. a BMI input box 144 for inputting a target BMI, a temperature input box 146 for inputting a target body temperature, a blood pressure input box 148 for inputting a target blood pressure, a sodium level input box 150 for inputting a target sodium level, a glucose level input box 152 for inputting a target blood glucose level, and a weight input box 154 for inputting a target weight. Note that entry boxes for still other biometric types as discussed herein may be included in the column 142 for a user to input a target for the respective type even if not specifically shown in reference to FIG. 4.

Still in reference to the UI 130, it also may include a selector element 156 selectable to automatically without further user input responsive thereto cause the CE device to e.g. communicate with one or more biometric sensors to receive current biometric information therefrom pertaining to the user to e.g. auto-fill one or more of the respective input boxes in column 132 such as e.g. a current blood pressure should a current blood pressure input box be presented in the column 132 (though not actually shown in FIG. 4 for clarity). Additionally, a selector element 158 is also shown that is selectable to automatically without further user input responsive thereto cause a list and/or history of previous plans to be presented on the CE device for the user to select therefrom a past plan to use again as a plan. Concluding the description of the exemplary UI 130, a submit selector element (though not shown) may be included for submitting the information entered to the input boxes.

Figure 5:
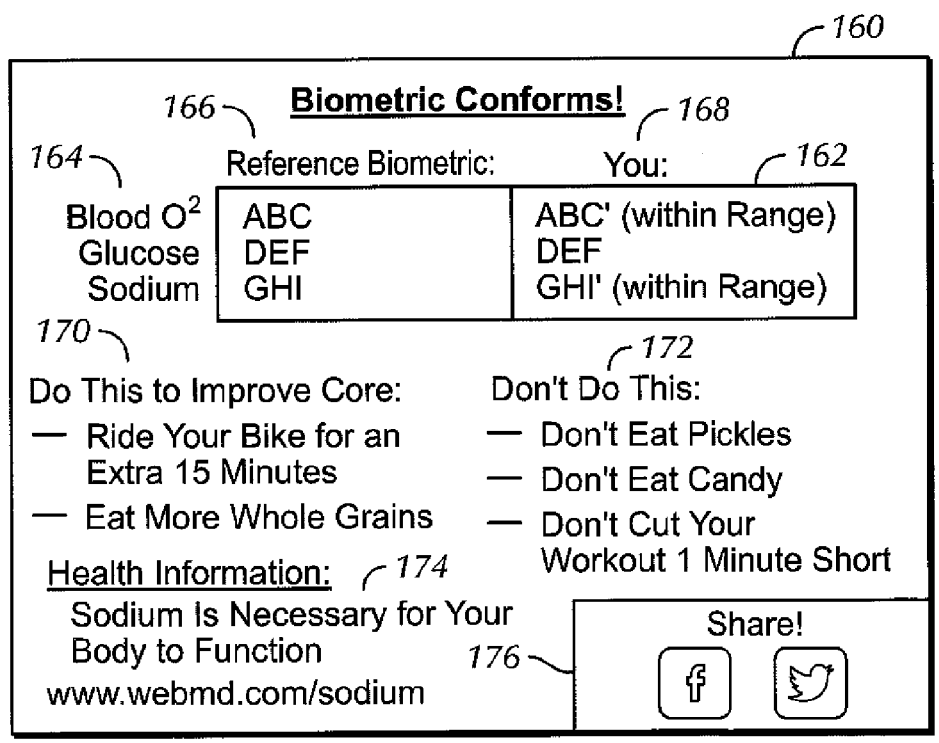

Now in reference to FIG. 5, an exemplary biometric status and/or target status UI 160 is shown that includes an indication that one or more (e.g. current) user biometrics conform to the user's desired health parameter and/or targets, and/or to reference biometrics. Accordingly, as shown in FIG. 5, an exemplary table 162 indicates in a first column 164 one or more biometric types, a second column 166 indicates a respective reference biometric and/or target provided by a user in accordance with present principles for the biometric type, and a third column 168 indicates respective (e.g. current) user-specific biometrics for the respective biometric types e.g. as determined based on input from one or more biometric sensors. Note that the biometrics indicated in the column 168 need not necessarily precisely match the respective reference biometric for a determination that the user's biometric conforms so long as e.g. the user's biometric is within a threshold of the reference biometric and/or within a reference biometric that includes a range as opposed to one specific number/parameter.

In addition to the foregoing, the UI 160 may also include a section 170 providing information on activities in which to partake to improve the user's biometrics even further and/or bring them even closer to the reference biometrics. For instance, the section 170 may provide instructions for the user to partake in one or more additional physical activities or behaviors, participate in those or other physical activities for a longer duration, eat particular foods and/or food classes/groups, etc. Likewise, a section 172 providing information on activities in which to not partake to improve the user's biometrics even further and/or bring them even closer to the reference biometrics is shown. The section 172 may include e.g. instructions for the user to refrain from one or more activities or behaviors, refrain from eating particular foods and/or food classes/groups, etc. Furthermore, note that although not shown, each respective piece of information in either column 170 or 172 may include an indication of the biometric type for which the information pertains and e.g. seeks to improve. For instance, a "Don't eat pickles" instruction in column 172 may be accompanied by the following: "This will improve your sodium levels."

Still in reference to the UI 160, it may also include a health information section 174 providing one or more pieces of health information that may or may not be unique and/or tailored to the user, such as e.g. health news on recently released health studies, selectable links to health-related websites that may be selected from the UI 160 to automatically without further user input cause the CE device to access the website and present it on the CE device, general health information pertaining to one or more of the biometric types from the column 164, etc. Last, the exemplary UI 160 includes one or more share selector elements 176 that are selectable to automatically without further user input share (e.g. a screen shot of) the UI 160 and/or information associated therewith over a social networking site corresponding to the selected element such as e.g. Facebook or Twitter.

Figure 6:
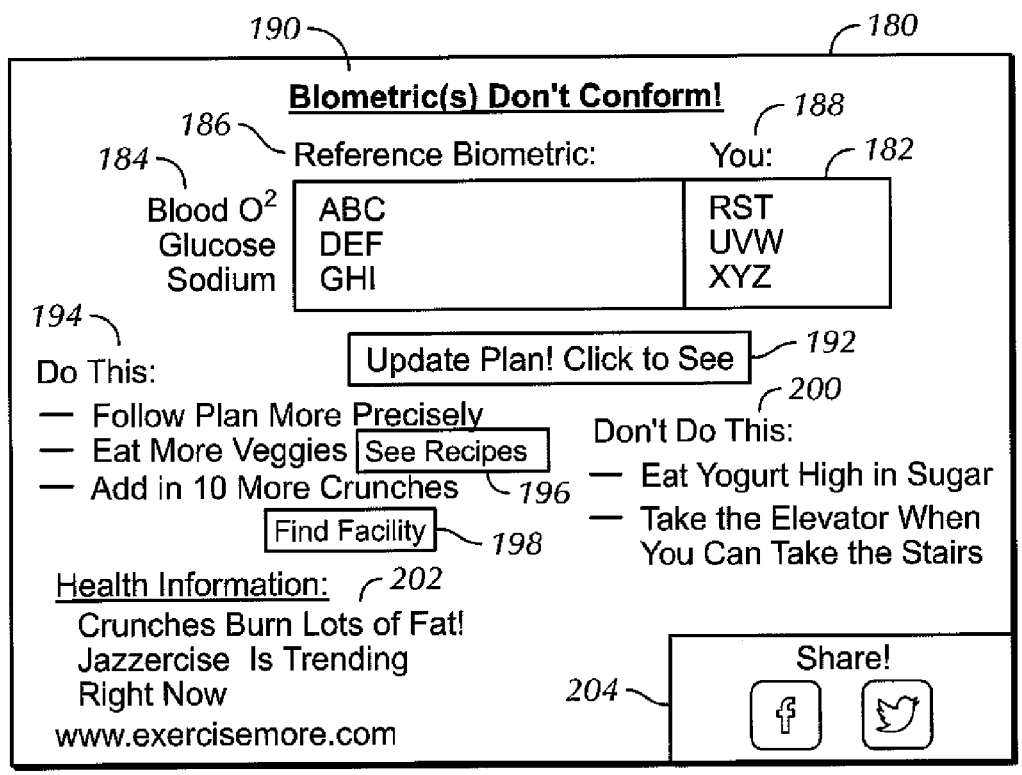

Moving on to FIG. 6, it shows an exemplary biometric status and/or target status UI 180 that includes an indication that one or more (e.g. current) user biometrics do not conform to the user's desired health parameter and/or targets, and/or to reference biometrics. Accordingly, as shown in FIG. 6, an exemplary table 182 indicates in a first column 184 one or more biometric types, a second column 186 indicates a respective reference biometric and/or target provided by a user in accordance with present principles for the biometric type, and a third column 188 indicates respective (e.g. current) user-specific biometrics for the respective biometric types e.g. as determined based on input from one or more biometric sensors, it being understood in contrast to FIG. 5 that the column 188 indicates user biometrics that do not conform to the reference biometrics from column 186. The UI 180 thus includes an alarm indication 190 such as a statement that is preceded and followed by exclamation points, though it is to be understood that an alarm in accordance with present principles that one or more of the user's biometrics fail to conform with a biometric target and/or reference biometric may additionally or instead be presented as an audible alarm (e.g. a police siren sound) and/or audible indication (e.g. spoken by a computerized voice and/or a voice determined by the user) of the reference biometrics that do not conform and/or information related thereto (e.g. which may be automatically presented responsive to a determination that a biometric does not conform and without user input).

Still in reference to the UI 180, a selector element 192 may also be presented thereon. The selector element 192 may be selectable to automatically without further user input responsive thereto cause an updated e.g. fitness plan to be (e.g. generated and/or) presented on the CE device relative to a previously determined plan from the CE device. Thus, the updated plan may be generated by the CE device responsive to determining that at least one of the user's current biometrics does not conform to the respective target and even that the user's current biometric fails to conform to where that user biometric was estimated by the non-updated plan to have been or reached at that point in time based on the user undertaking actions in conformance with the initial plan that was generated. For instance, a user's body may burn calories at a slower rate for the same exercise than a reference biometric for the average number of calories that the general public is estimated to burn for the exercise. In such an instance, the logic may determine based on input from one or more biometric sensors that the user thus needs to engage in further exercise to burn the same amount of calories as the reference biometric and therefore that the user's plan should be adjusted accordingly to nonetheless still reach the reference biometric and/or the user's target given the user's relatively less calorie-burning physical output.

Continuing the description of the UI 180, it may also include a section 194 providing information on activities in which to partake to improve the user's biometrics to thus bring them into conformance with the plan and/or reference biometric in accordance with present principles. Note further that the section 194 may include selector elements corresponding to respective entries in the section 194 that e.g. provide interactive features.

For instance, an entry instructing the user to eat more vegetables may be accompanied by a see recipes selector element 196 selectable to automatically without further user input responsive thereto cause the CE device to access (e.g. from a cooking website) and then present on the CE device one or more recipes for which what is indicated in the entry is used as an ingredient. In the present exemplary instance, selection of the selector element 196 may cause one or more recipes that require vegetables to be presented for the user to thus e.g. prepare a meal including vegetables to thus attempt to conform to the indication of food to eat to improve the user's biometric(s).

Likewise, a location selector element 198 selectable to automatically without further user input responsive thereto cause the CE device to access (e.g. a list of gyms on the Internet) and then present on the CE device indications of one or more nearby gyms and/or fitness facilities (e.g. based on GPS coordinates determined by the CE device using a GPS receiver thereon), which may be included next to an indication of a physical activity in which to undertake so that the user may e.g. go to one of the facilities indicated to undertake in the physical activity. Before moving on, also note that a section 200 providing information on activities in which to not partake to improve the user's biometrics in accordance with present principles is shown.

Still in reference to the UI 180, it may also include a health information section 202 in accordance with present principles for providing one or more pieces of health information that may or may not be unique and/or tailored to the user. Last, the exemplary UI 180 includes one or more share selector elements 204 in accordance with present principles that are selectable to automatically without further user input share (e.g. a screen shot of) the UI 180 and/or information associated therewith over a social networking site corresponding to the selected element such as e.g. Facebook or Twitter.

Now in reference to both FIGS. 5 and 6, note that one or more of the elements, indications, information, recommendations, etc. from the respective UIs 160 and 180 may be combined with each other into a single UI though not specifically shown. Thus, for instance, should some of the user's biometrics for various biometric types conform to the user's targets while others do not, indications of both those biometrics that conform and those that do not may be presented on a single UI. Also in reference to both FIGS. 5 and 6, note that the respective columns 166 and 186 for reference biometrics may additionally or instead indicate the user's indicated target biometric (e.g. if different from the reference biometric).

Without reference to any particular figure, it is to be understood that exercise plans in accordance with present principles may in some embodiments be generated at a server and provided to a CE device rather than being generated at the CE device itself.

Furthermore, present principles recognize that although much of the foregoing has been directed specifically to exercise routines, present principles may apply not only to exercising but also other activities not necessarily commonly construed as "exercises" such as walking down the street or sitting with a particular posture at a desk.

Accordingly, it may now be appreciated that as health and wellness is increasingly in the forefront of our everyday lives, present principles meet the increased desire for users to know more about how well their bodies are functioning and what changes can be made to optimize their body biometrics and functions to thus keep them as close to ideal and/or health as possible.

Thus, in one embodiments present principles may be undertaken by a wearable diagnostics smart device that is configured to track and monitor e.g. full bodily functions including, but not limited to, temperature, blood pressure, oxygen consumption, calories in and out, sugar levels, sodium levels, sleep patterns, mood/energy (e.g. using a mood sensor), etc. The wearable smart device with sensors measuring biometrics of the user may help a user to set and track goals, as well as warn the user when the user's levels are off and/or out of sync (e.g. with healthy normals). With this information, the user may subsequently make informed changes to improve their health by e.g. following instructions and/or recommendations provided by the wearable smart device. Furthermore, the information provided to the user (e.g. on a UI such as the UIs 160 and 180 described above) may change and/or report out in real time information (e.g. biometric information) in accordance with present principles, and can also sync with other devices to provide more robust reporting (e.g. for viewing on more than one of the user's devices such as a tablet even if the biometrics were taken by the wearable device). Such devices may also e.g. provide recommendations to the user such as types of foods, recipes, exercises, fitness facilities, etc.

Thus, such a wearable smart device may be thought of as a portable diagnostics device that tracks and reports physical activity for a user, tracks consumption and operating levels, and provides recommendations on food and activities to help balance and optimize overall health and wellness. Things that may be tracked include e.g. calories in (e.g. consumed) and out (e.g. used or burned), temperature, blood pressure, heart rate, oxygen consumption, sugar and sodium levels, etc.

Before concluding the detailed description, it is to be understood that although e.g. an application for undertaking present principles may be vended with a CE device for undertaking present principles, present principles also apply in instances where one or more of the foregoing features and/or an application including software code for undertaking present principles may be e.g. downloaded from a server to a device over a network such as the Internet.

While the particular DEVICES AND METHODS FOR HEALTH TRACKING AND PROVIDING INFORMATION FOR IMPROVING HEALTH is herein shown and described in detail, it is to be understood that the subject matter which is encompassed by the present invention is limited only by the claims.

What is claimed is:

1. A device comprising:
at least one computer memory that is not a transitory signal and that comprises instructions executable by at least one processor for:
receiving input pertaining to at least a first health parameter;
monitoring at least one biometric of a user;
determining whether the user's biometric conforms to the first health parameter;
in response to determining that the user's biometric conforms to the first health parameter, providing an indication that the biometric conforms to the first health parameter and providing information pertaining to a reference biometric, the reference biometric being of the same biometric type as the user's biometric;
in response to determining that the user's biometric does not conform to the first health parameter, providing a recommendation for conforming to the first health parameter; and
providing an indication of at least one specific sustenance to refrain from consuming to reach a biometric target.

2. The device of claim 1, wherein the input pertaining to the first health parameter is received from the user, and wherein the user's biometric does not conform to the first biometric at or around the time of receiving the input.

3. The device of claim 1, where the information pertaining to the reference biometric includes the reference biometric, and wherein the reference biometric is derived by the device from information from a public health agency website.

4. The device of claim 1, where the information pertaining to the reference biometric includes the reference biometric, and wherein the reference biometric is derived by the device from information from a government website.

5. The device of claim 1, where the information pertaining to the reference biometric includes the reference biometric, and wherein the reference biometric is a biometric average of plural persons of the same age and gender as the user.

6. The device of claim 1, wherein the determining whether the user's biometric conforms to the first health parameter includes comparing the user's biometric against the first health parameter and determining whether the user's biometric is within a threshold of the first health parameter.

7. The device of claim 1, wherein the device is a first device, and wherein the indication is provided on a user interface (UI) presented on a second device different from the first device.

8. The device of claim 1, wherein the device is a first device, wherein the recommendation is provided on a user interface (UI) presented on a second device different from the first device, and wherein the UI includes a link to a website pertaining to health information.

9. The device of claim 1, wherein the biometric type is one of: blood oxygen level, glucose level, sodium level, and resting heart rate.

10. The device of claim 1, wherein the recommendation includes an instruction for the user to alter the user's physical activity in at least one respect.

11. The device of claim 1, wherein the recommendation includes an indication of sustenance to consume.

12. The device of claim 1, wherein the user's biometric is monitored at least in part based on signals from one or more biometric sensors configured to gather biometric information from the user.

13. A method, comprising:
receiving a biometric target from a person;
receiving at least one signal from a biometric sensor sensing a biometric of the person;
based at least in part on the signal, determining whether the biometric target has been reached; and
responsive to a determination that the biometric target has not been reached, providing at least a first indication that the biometric target has not been reached; and
providing an indication of sustenance to refrain from consuming to reach the biometric target.

14. The method of claim 13, further comprising:
responsive to the determination that the biometric target has not been reached, providing at least one instruction to the person for reaching the biometric target.

15. The method of claim 14, wherein the instruction includes an indication of physical activity in which to refrain from engaging to reach the biometric target.

16. The method of claim 13, wherein the first indication is an alarm presentable on a device associated with the user at a time indicated by the user at which the alarm is to be presented responsive to the biometric target not being reached by the time.

17. The method of claim 13, wherein the target is a biometric range for a biometric type.

18. A device, comprising:
- at least one computer memory that is not a transitory signal and that comprises instructions executable by at least one processor for:
- receiving at least one physical fitness target from a user;
- determining at least one biometric range for which at least one biometric of the user is to reach to conform to the physical fitness target; and
- providing a fitness plan to the user to reach the physical fitness target at least in part by:
- accessing an average time to incrementally alter the biometric type of the biometric when undertaking a particular activity;
- determining a number of increments the biometric of the user is from the biometric range; and
- multiplying the average time by the number to render a total time, and wherein the fitness plan includes an indication of the total time the particular activity is estimated to be undertaken to reach the physical fitness target.

* * * * *